United States Patent [19]

Michaelson et al.

[11] Patent Number: 5,223,464

[45] Date of Patent: * Jun. 29, 1993

[54] PROCESS FOR REGENERATING A CATALYST USED IN PRODUCTION OF OLEFINS BY CATALYTIC ETHER DECOMPOSITION

[75] Inventors: Robert C. Michaelson, Kinnelon; Gustavo Cerri, Boonton, both of N.J.

[73] Assignee: Exxon Chemical Patents Inc., Linden, N.J.

[*] Notice: The portion of the term of this patent subsequent to Aug. 27, 2008 has been disclaimed.

[21] Appl. No.: 683,769

[22] Filed: Apr. 10, 1991

Related U.S. Application Data

[62] Division of Ser. No. 387,162, Jul. 31, 1989, Pat. No. 5,043,518.

[51] Int. Cl.⁵ .................... B01J 21/20; C07C 1/00
[52] U.S. Cl. ........................ 502/33; 502/29; 585/639; 585/640
[58] Field of Search .............. 502/33, 30; 585/639, 585/640

[56] References Cited

U.S. PATENT DOCUMENTS 1,933,508 10/1933 Peck .................................... 502/33

FOREIGN PATENT DOCUMENTS 132652 7/1985 Japan ................................... 502/33

Primary Examiner—Paul E. Konopka
Attorney, Agent, or Firm—Linda K. Russell

[57] ABSTRACT

A process for regenerating a catalyst which involves washing a catalyst with a liquid at a temperature within the range of about 50° C. to about 70° C. for a time sufficient to remove foulants thereby recovering catalyst activity. The wash liquid is preferably a member selected from the group consisting of ethers, alcohols and mixtures of ethers and alcohols wherein the ether is a tertiary alkyl ether, preferably selected from the group consisting of tertiary amyl methyl ether and methyl tertiary butyl ether, and wherein the alcohol is preferably selected from the group consisting of tertiary butyl alcohol and methanol. The catalyst is preferably a clay treated with an acid selected from the group consisting of hydrofluoric acid, hydrochloric acid and mixtures of hydrofluoric and hydrochloric acid, wherein the clay is preferably selected from the group consisting of montmorillonite, kaolinite, attapulgite, bentoninte and natural clay.

23 Claims, 2 Drawing Sheets

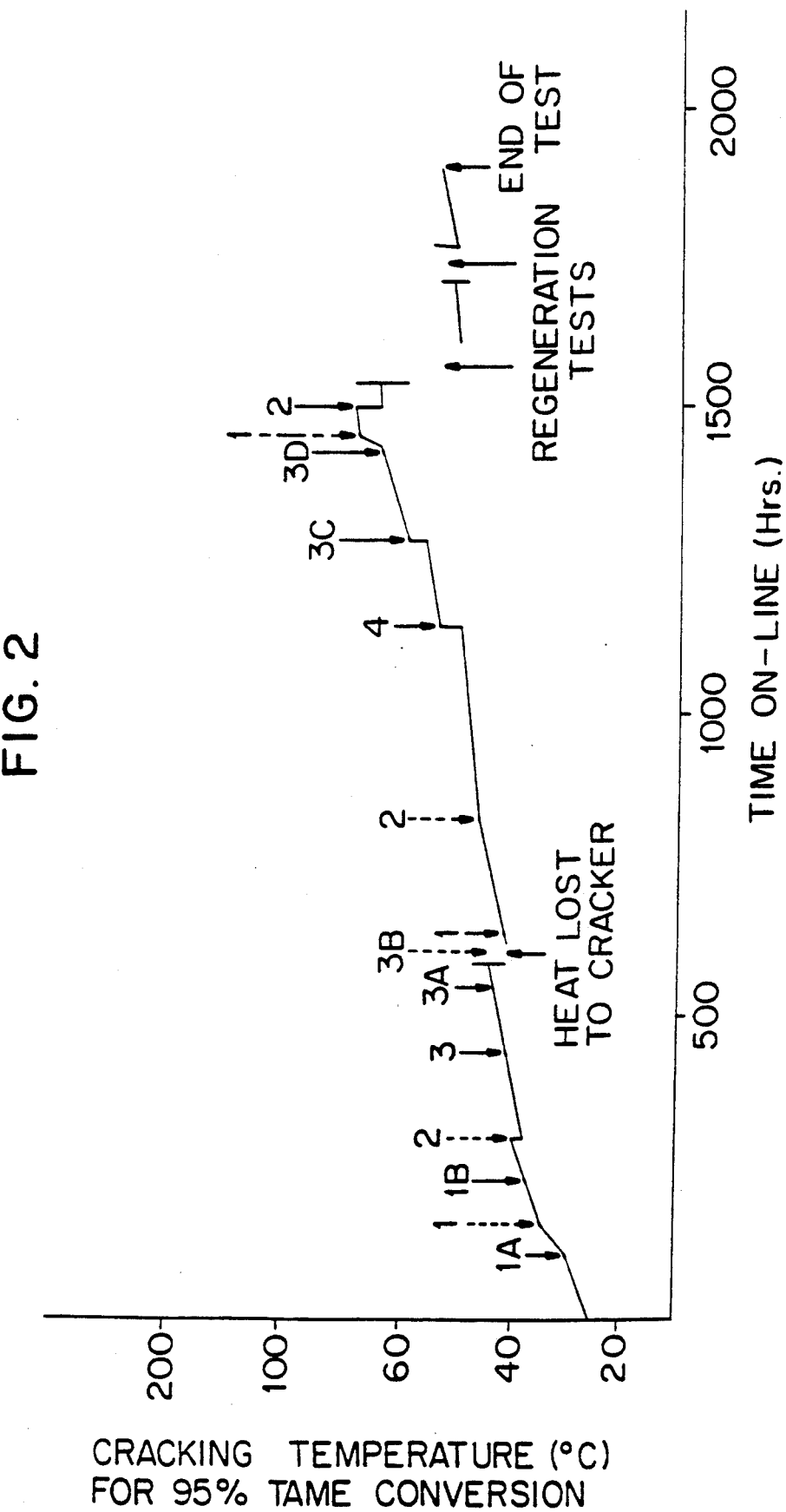

PROCESS FOR REGENERATING A CATALYST USED IN PRODUCTION OF OLEFINS BY CATALYTIC ETHER DECOMPOSITION

This is a division of application Ser. No. 387,162, filed Jul. 31, 1989 now U.S. Pat. No. 5,043,518.

FIELD OF THE INVENTION

The present invention relates to methods for producing olefins by catalytic decomposition of ether precursors, ethers, alcohols and mixtures thereof. Specifically, the present invention is directed to processes for regenerating catalysts and particularly decomposition catalysts used in methods for decompositions ethers, alcohols and mixtures thereof to produce olefins.

DISCUSSION OF BACKGROUND AND/OR MATERIAL INFORMATION

Tertiary olefins. are in general commercially produced by the sulfuric acid extraction of such olefins from mixtures containing them obtained e.g., by steam cracking of petroleum feeds.

Tertiary olefins may be prepared by reacting them selectively from such feeds with a primary alcohol in the presence of an acid catalyst to produce the corresponding alkyl tert-alkyl ethers; only the tert-alkyl ethers are formed since the secondary olefins react very slowly and the primary olefins are completely inert. Such alkyl tert-alkyl ethers may then be easily separated and subsequently decomposed back to the tertiary olefins and the primary alcohol.

Although it is disclosed that the clay of the catalyst is preferably washed first with water and then with methanol before calcining, this washing refers to that which is conducted after the clay is reacted with the acid, and does not refer to a washing which is conducted for the purpose of regenerating a deactivated catalyst which has been taken off-line due to becoming contaminated with foulants, after some time on stream.

U.S. Pat. No. 2,784,238, discloses regenerating a clay catalyst by washing the catalyst with a polar oxygenated solvent until the resins absorbed on the catalyst are dissolved. However, the clay catalyst is used in the production of resorcinals by the decompositions of hydroperoxides, and does not regenerate the catalyst in situ.

U.S. Pat. Nos. 3,472,786 and 4,469,805, disclosed the use of a methanol wash to regenerate clays used as absorbents for treating hydrocarbons; however, the clays are not disclosed as being useful as catalysts for any reaction.

Japanese Patent No. JP60-075331, discloses the regeneration of a layered clay catalyst by washing the clay with an aqueous mixture including 50-98% of an organic medium, such as methanol or ethanol, and discloses that the layered catalyst is for use in dewatering reactions, esterification, etherification and alkylization reactions.

Japanese Patent No. JP87-054540, washes a supported hydrogenation catalyst.

A number of methods have been proposed for producing tertiary olefins from alkyl tert-alkyl ethers using various catalysts.

U.S. Pat. No. 4,398,051, for example, uses aluminum compounds supported on silica or other carriers. U.S. Pat. No. 4,320,232 employs phosphoric acid on various supports. British Patent No. 1,173,128 uses metal-containing weakly acidic components on a carrier of 20 $M^2/gm$ surface area. U.S. Pat. No. 4,398,051 attempts to produce tertiary olefins from alkyl tert-alkyl ethers utilizing carriers alone in the decomposition of methyl tertiary butyl ether.

U.S. Pat. No. 4,691,073, MICHAELSON, discovered that high purity olefins are obtainable in extremely high yields over a sustained period by bringing alkyl tert-alkyl ethers into contact with a specified catalyst, i.e., clays treated with hydrofluoric acid and/or hydrochloric acid. Although a counter-flow stream of ether feed is disclosed, this is not done to substantially regenerate a catalyst in a fixed bed isothermal reactor.

It is known that tertiary olefins may be prepared by reacting them selectively from petroleum feeds with a primary alcohol in the presence of an acid catalyst to produce the corresponding alkyl tert alkyl ethers. Such alkyl tert-alkyl ethers may then be separated and subsequently decomposed back to the tertiary olefins and the primary alcohol.

U.S. Pat. No. 4,447,668, prepares isobutene or isoamolene from alkyl tertiary butyl ether or alkyl tertiary-amyl ether wherein a fixed bed cationic acidic exchange resin is used in a catalytic distillation process.

All these processes suffer from disadvantages. Among these disadvantages is that known catalysts do not have good catalyst life because higher temperatures, which eventually become limiting, are required to maintain high conversion of the alkyl tert-alkyl ethers. Additionally, larger amounts of the dialkyl ether by-product are produced as the catalyst ages with the disadvantage indicated above. This lack of good catalyst life may be due to the instability of the catalyst to high temperature being required for good conversion thus promoting fouling, to the catalyst itself promoting fouling, or to any or all of these. Also, a number of the catalysts, such as resins, cannot be regenerated after use.

SUMMARY OF THE INVENTION

The present invention is directed to the process for regenerating a vapor phase decomposition catalyst which involves washing a catalyst which has been contaminated with foulants with a liquid at a temperature within the range of about 40° C. to about 80° C. for a time sufficient to remove foulants thereby recovering catalyst activity. The temperature at which the catalyst is washed is preferably within the range of about 45° C. to about 75° C., with temperatures within the range of about 50° C. to about 70° C. being most preferred.

Related to this, the present invention is also directed to a process for regenerating a fouled catalyst which involves washing a catalyst which has been contaminated with foulants with a liquid selected from a group of hydrocarbons in liquid form which are the same hydrocarbons in the vapor phase which are decomposed over the catalyst in the production of olefins. In accordance with the present invention, therefore, regeneration wash liquids are preferably selected from the group consisting of ethers, alcohols and mixtures of ethers and alcohols at a temperature and for a time sufficient to remove foulants and recover catalyst activity.

In a preferred embodiment in accordance with the present invention, the process for regenerating a decomposition catalyst, which has become fouled with olefin derived polymers and other materials involves washing a deactivated acid catalyst with a liquid selected from the group consisting of ethers, alcohols and mixtures of ethers and alcohols at a temperature within the range of about 50° C. and 70° C. to remove the polymer and other materials and recover substantial catalyst activity so as to result in a regenerated catalyst whereby the temperature required during cracking when the regenerated catalyst is put back on line at least about 15° C. lower than the highest temperature required during cracking before the deactivated catalyst was taken off line and subjected to regeneration in accordance with the present invention.

The processes for regenerating catalysts in accordance with the present invention have been discovered to be particularly useful for regenerating catalysts used in a catalytic decomposition process for producing olefins. Thus, the present invention also relates to catalytic decomposition processes for producing olefins which involve decomposing a hydrocarbon fluid stream, composed of at least one member selected from the group consisting of ethers, alcohols and mixtures of ethers and alcohols, preferably in a vapor phase, over a decomposition catalyst under conditions including a temperatures sufficient to support a reaction for converting these members to olefins; discontinuing the reaction over the decomposition catalyst when the temperature at the outlet of the reactor increases to an objectionably high temperature which is indicative of a deactivated catalyst; regenerating the deactivated catalyst by exposing the deactivated catalyst to a liquid which includes at least one member of the hydrocarbon fluid stream at a temperature within the range of about 50° C. to about 70° C. for less than about 35 hours, preferably by back-flushing, to remove contaminants and recover catalyst activity to result in a regenerated catalyst; and placing the regenerated catalyst back on line and passing hydrocarbon fluid stream over the regenerated catalyst at a temperature of at least about 15° C. lower than the objectionably high temperature indicative of a deactivated catalyst to produce olefins.

The regeneration in accordance with the present invention is preferably performed in situ in the reactor, preferably by back-flushing the regeneration wash liquid through the reactor from the outlet end. Subsequent to exposing the deactivated catalyst, the reactor is preferably flushed with an inert gas, such as nitrogen ($N_2$), again more preferably by back flushing the reactor with the inert gas, before the reactor containing the regenerated catalyst is brought back on line.

In addition, the present invention is also directed to catalyst for decomposing a member selected from the group consisting of ethers, alcohols and mixtures of ethers and alcohols to produce olefins which have been regenerated to remove foulants and recover catalyst activity exposing, preferably by back flushing with, to a liquid selected from the group consisting of such ethers, alcohols and mixtures of ethers and alcohols at a temperature within the range of about 50° C. to about 70° C. for less than about 30–40 hours, and most preferably less than about 50 hours and preferably less than about 30 hours, i.e., between about 10–30 hours.

In accordance with the present invention, the ether is preferably a tertiary alkyl ether, which is more preferably selected from the group consisting of tertiary amyl methyl ether (TAME) and methyl tertiary butyl ether (MTBE), and preferably where the tertiary alkyl ether is tertiary amyl methyl ether (TAME).

Alcohols found to be suitable for purposes of the present invention are members selected from the group consisting of tertiary amyl alcohol (TAA), tertiary butyl alcohol (TBA), and methanol (MeOH) and mixtures of at least two members selected from the groups consisting of TAA, TBA and methanol, with methanol being preferred.

The catalyst suitable for the catalytic decomposition which is regenerated in accordance with the present invention are preferably acid catalysts. A preferred acid catalyst for purposes of the present invention is a clay treated with an acid selected from the group consisting of hydrofluoric acid, hydrochloric acid and mixtures of hydrofluoric acid and hydrochloric acid, with clays treated with hydrofluoric acid being most preferred. The clays which are treated with the acid which have found to particularly suitable for catalytic decomposition and regeneration in accordance with the present invention include montmorillonite, kaolinite, attapulgite, bentoninte and natural clay, with natural clay being particularly preferred along with attapulgus clay and montmorillonite clay. The catalyst preferably has a surface area above 40 $m^2$/gm, and a surface area preferably in the range of about 60 $m^2$/gm to about 400 $m^2$/gm.

BRIEF DESCRIPTION OF THE DRAWINGS

FIG. 2 is a graph showing cracking temperatures necessary to achieve 95% TAME conversion both before and after regeneration of the catalyst.

DETAILED DESCRIPTION

Figure 1:
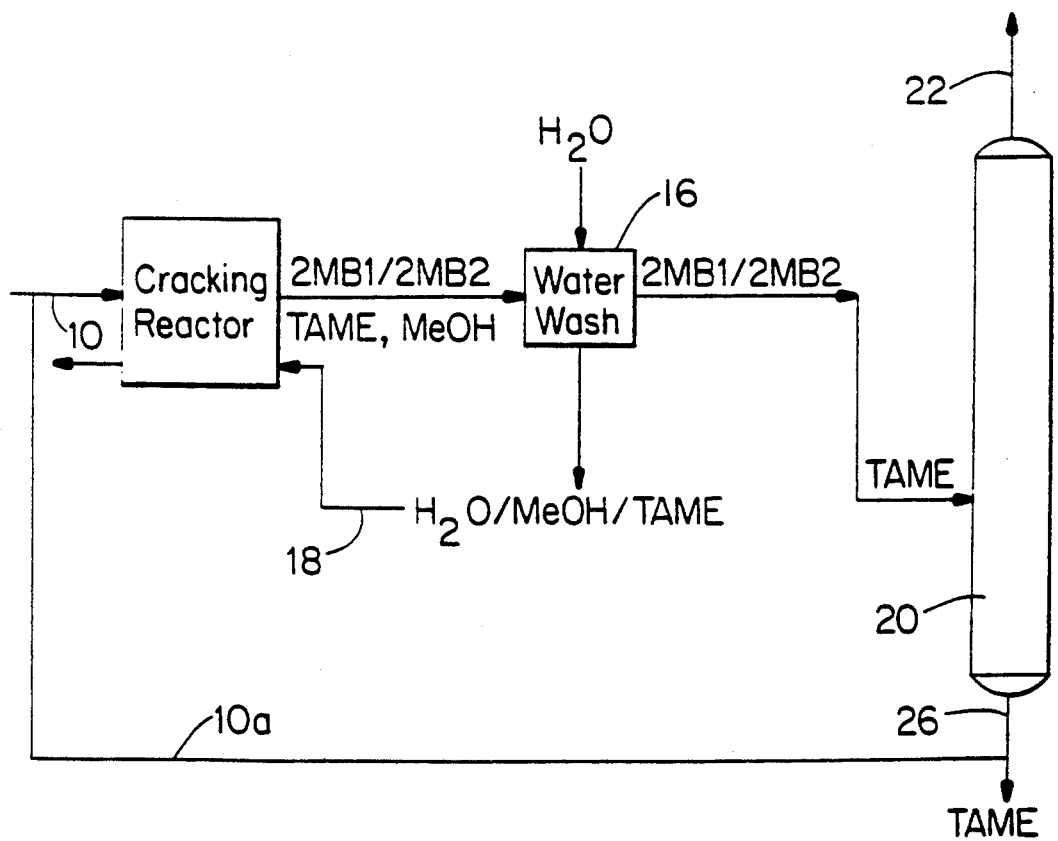
FIG. 1 shows a schematic representation of a process for producing isoamylene, which involves catalyst regeneration using liquid ether and alcohols in accordance with the present invention, used in an ether composition process.

The present invention broadly relates to processes that produce olefins by decomposition of an ether precursor, for example, isobutylene from MTBE, isoamylene from TAME, and isobutylene from TBA.

The catalytic decomposition reaction required to produce an olefin by cracking or decomposing an ether precursor is typically carried in the gas phase over an acidic catalyst which has been observed to produce heavy polymers and other materials which decompose over the active sites of the catalyst thereby contributing to catalyst deactivation. Consequently, in such processes for producing an olefin by catalytic decomposition, the cracking catalyst run length is reduced by fouling. Although not wishing to be bound by any particular theory, it is believed that such contamination, or deactivation of the cracking catalyst, is due at least in part to fouling by deposition of polymers, such as heavy polymers, over the active sites of the catalyst.

The present invention, therefore, is directed to methods for regenerating decomposition catalysts in processes that decompose an ether, alcohol or mixtures thereof, to produce an olefin wherein the regeneration of the catalyst is performed at relatively low temperatures in order to extend the run length.

The method in accordance with the present invention has been discovered to remove foulants or contaminants thereby recovering at least a part or substantially all of the original catalyst activity by washing the fouled catalyst with components of the hydrocarbon fluid feedstream, in the liquid phase, which are subjected to the catalytic decomposition process in the production of olefins. In this regard, it has been discovered that the liquid phase of feedstock components, i.e. the ether, alcohol, or mixtures thereof, dissolves at least part, if not substantially all, of the polymeric and other material which may have become deposited over the active sites of the catalyst thereby reexposing the catalytic sites.

An advantage of the regeneration method in accordance with the present invention is that the regeneration can be performed at relatively low temperatures, i.e., within the range of about 40° C. to about 80° C., preferably within the range of about 45° C. to about 75° C., and more preferably within the ranges of about 47° C. to about 55° C. and about 50° C. to about 70° C. This is in contrast to conventional regeneration procedures which require relatively high temperatures of 500° C. or more, for example used in traditional air or coke burn steps.

Another advantage of the method for regenerating catalysts in accordance with the present invention is that the regeneration wash liquid used for this purpose, i.e., the ether, alcohol or mixtures of the ether or alcohol, are preferably the hydrocarbons which are used in the vaporized stream of hydrocarbon fluid being passed over the decomposition catalyst. Thus, if any regeneration wash liquid were to remain, the residue would not contaminate the purity of the feedstock. So that there is even less chance that the product will be contaminated with any residual regeneration wash liquid which happens to remain on the regenerated catalyst the washed catalyst is flushed with an inert gas, such as nitrogen, before the regenerated catalyst is brought back on line in the catalytic reaction zone.

Moreover, inasmuch as the product stream from the reactor which is washed with water prior to being passed to the distillation column contains the ether and/or the alcohol originally introduced into the decomposition reactor in addition to the desired product, the ether and/or alcohol removed by water washing can be recovered and recycled to the catalyst regeneration stage and used as the regeneration wash liquid for this purpose.

As previously mentioned, the most preferred tertiary alkyl ether for purposes of production of olefins is tertiary amyl methyl ether, i.e., TAME, when isoamylene is being produced; and methyl tertiary butyl ether, i.e., MTBE, when isobutylene is being produced, although other tertiary amyl alkyl ethers may be used. Depending on the particular ether, the alcohol which is derived from the disassociation of the ethers may be ethanol, isopropanol, tertiary butyl alcohol and the like, although methanol results when TAME is processed.

Suitable catalysts and conditions used in the cracking step of this stage of the process are disclosed in U.S. Pat. No. 4,691,073 MICHAELSON, commonly owned with this application, the disclosure of which is hereby incorporated by reference thereto. Briefly, the catalyst utilized in the present invention may be prepared by reacting a naturally occurring or synthetic clay with hydrofluoric acid (HF) or hydrochloric acid (HCl) followed by calcining. The reacting or incorporation of HF or the HCl with the clay can be accompanied by any means, such as contacting the clay with anhydrous HF or HCl or by impregnation of the clay with an aqueous acid, for example, a mixing method equilibrium absorption method, evaporation-to-dryness method, spray drying and the like. Preferably the clay is reacted with 1.0 to 70 wt. %, preferably 20 to 50 wt. % hydrofluoric acid or 1.0 to 30% to 37%, preferably 20 to 30 wt. % hydrochloric acid at temperatures of 0° C. to 50° C., preferably 10° C. to 30° C. for 30–120 minutes. The amount of the acid is 0.001 to 1.0, and preferably 0.01 to 0.10 gm anhydrous acid/gram clay. Following the reaction, the fluid is decanted and the clay is then preferably washed first with water and then with alcohol before calcining. The calcining temperature is selected so as to achieve a highly active high-surface area catalyst of a moisture content of less than 5 wt. %. Preferably temperatures are 250° C. to 1,000° C., and more preferably 400° C. to 700° C. The calcination is generally carried out in air, but an atmosphere of an inert gas, for example nitrogen, carbon dioxide, and argon, in addition to steam or mixtures thereof may also be used. The time for calcination is generally 0.1 to 24 hours, and preferably 0.5 to 10 hours, although the time depends upon the calcination temperature. The amount of the flourine or chlorine compounds supported on the carrier is 0.1 to 100 parts by weight of the carrier and preferably 1.5% to 6.0%. Examples of the carrier containing silicon oxides include silica, montmorillonite, kaolinite, attapulgite, bentoninte and acid clay, in addition to silica alumina, silica-zirconia, silica-magnesia and their mixtures. The silica may be either in the form of the gel or sol. A particularly preferred carrier is one prepared from attapulgite or montmorillonite-type minerals. The surface area of the carrier is preferably more than $1_m{}^2/gm$, and more preferably above $40_m{}^2/gm$. Preferred surface areas after calcination are in the range of $60_m{}^2/gm$ to $400_m{}^2/gm$. The most preferred catalyst, however, is hydrofluoric acid treated attapulgite clay. It has been discovered that this catalyst is particularly effective at lower cracking temperature, i.e. 125° C.–130° C., and produces only about 0.05 wt. % dimethyl ether at 98% TAME conversion.

As disclosed in U.S. Pat. No. 4,691,023, the performance of the catalyst used in the present invention is superior in activity and selectivity to the more conventional catalysts. Although details are not clear, this may be because of the unique mixture of acids and basic sites affordable by these materials. In addition, the catalyst of this invention provides extended catalytic life which is highly important for industrial use.

The extended catalyst life in the present invention process is due at least in part to the high stability of HF or HCL treated clay as opposed to other acid treated clays.

The reaction of decomposition of the tert-alkyl ethers, in accordance with the present invention is disclosed, for example, in U.S. Pat. No. 4,691,073, the disclosure of which is incorporated in its entirety by reference thereto herein. In this regard, catalytic decomposition takes place with good yields under atmospheric pressures, but it is preferred to operate under slightly superatmospheric pressures so as to permit the use of cooling water without any other expedient to carry out the condensation of the products which are obtained.

The working pressures are generally ranging from 1 to 20 kilograms/sq. cm absolute; and preferably under a pressure which is at least equal to the vapor pressure of isoamylenes and TAME at the condensation temperature which is foreseen. High temperatures, i.e. up to 60 psia and high methanol, i.e., up to 10% in the feed have been observed to cause only a slight TAME increase in the cracking temperatures because equilibrium is favorable to total conversion, although it is believed that the catalyst fouls more rapidly at the higher pressures.

The reaction is carried out at a temperature below 250° C., and preferably in the range of 100° C.–250° C., and more preferably in the range of 110° C.–230° C. The reaction is carried out at a spacial velocity, expressed in terms of volume of liquid per volume of catalyst per hour (LHSV) ranging between 0.5 and 30, and preferably of 1 to 5. Preferably, conditions are selected to obtain conversions to the isoamylenes of tert-alkyl ethers of 80% and preferably 90%. With this in mind, the normal operating temperature of the cracker reactor should be maintained within the range of 120° F. to 170° F. The cracking temperature is preferably controlled so as to maintain preferably at least about 95% TAME conversion. However, it is necessary to raise the cracking temperatures during the course of the conversion to an extent whereby catalyst fouling is observed during the course of the run length. A run length of about 3 months is expected before reaching an objectionably high temperature of about 170° C.

The feedstream may also be obtained via decomposition of TAME as described in U.S. Pat. No. 4,691,073, and controlling the TAME conversion such that the desired amount of TAME remains in the isoamylene stream after water washing to remove methanol. Alternatively, a $C_5$ hydrocarbon stream containing isoamylenes may be reacted with methanol over an acidic catalyst to convert 2-methyl butene 1 (2MB1) and 2-methyl butene 2 (2MB2) to TAME for use in forming the mixture.

Referring now to FIG. 1, a schematic system is shown, for converting tertiary alky ethers to olefins which includes the regeneration of the catalyst in accordance with the present invention. A hydrocarbon fluid feed stream 10 containing at least about 90 wt. % tertiary amyl methyl ether (TAME) is vaporized before being introduced to a cracking reactor 14. As illustrated, the TAME may be recycled from distillation column 20 a bottom fraction, to make up at least a portion of feedstream 10. Alternatively or additionally, TAME may be provided from a separate source of supply. For example, the TAME may be recovered from a $C_5$ hydrocarbon stream by reacting the $C_5$ hydrocarbon stream with methanol over an acidic catalyst to convert the 2-methyl-1-butene and the 2-methyl-2-butene contained in the $C_5$ hydrocarbon stream to tert-amyl methyl ether (TAME).

The cracking reactor 14 is provided with an acid-treated clay catalyst in the reactor tubes, as previously described herein, and is heated to a temperature within the range of 120° C. to 170° C. The effluent or product stream leaving the cracking reactor is composed of isoamylenes, i.e. 2MB1 and 2MB2, in a ratio of between about 1:2 to 5 and preferably in a ratio of 1:5, unreacted TAME, and methanol (MeOH). The product stream may then be washed with water to separate the methanol from the isoamylene and unreacted TAME in water wash stage 16. The cracking catalyst as it is fouled with contaminants or foulants, such as decomposed polymer or other material, becomes deactivated and requires a higher temperature in order to permit the conversion to proceed. When the temperature required for conversion reaches an objectionably high temperature within the range of about 170° C. to 200° C., regeneration of the catalyst becomes necessary. In accordance with the present invention, as discussed above, this is done using preferably the same ethers and alcohols, although in a liquid state, used in the cracking process, i.e., in this case TAME and methanol. In order to regenerate the catalyst, the vapor feed to the reactor is stopped and the reactor is cooled. The ethers and alcohols, as liquids, may be rerouted to enter the reactor or may be recovered from the wash water discharged from washing stage 16 and recycled as the regeneration was liquid during catalyst regeneration. This is preferably accomplished by back flushing the reactor with the regeneration was liquid. Accordingly, the liquid regeneration TAME feed may be rerouted, or recovered TAME and methanol may be recycled, to enter the reactor at the outlet and pass through the preheater, not shown in FIG. 1, also from the outlet to the inlet and to the product receiver. The reactor, and the preheater, thus are back flushed in this manner with the regeneration wash liquid, i.e., TAME, methanol or mixtures of TAME and methanol at a temperature of about 40°-50° C. and preferably at the same feed rate as during normal cracking.

The back-flush with the regeneration wash liquid was conducted for up to about 50 hours. During this time, it was observed that the effluent was initially relatively dark brown in color but became progressively lighter until the regeneration wash liquid was substantially clear, similar to the clarity of tap water, after about 30–40 hours. Regeneration in accordance with the present invention, however, can be effected preferably by washing the catalyst with regeneration wash liquid for less than about 30 hours.

The back-flush technique for washing the deactivated catalyst with the regeneration wash liquid is preferred because using a forward flush has been found to be not as successful in removing the foulants or contaminants which become deposited on the active sites of the catalyst. In this regard, the foulants and contaminants which become deposited on the catalyst as it becomes deactivated may be polymers; as such, the forward flush may carry the polymer and the polymer precursors, which are believed to be formed in the preheater, into the catalyst. Although not wishing to be bound by any particular theory, it is believed that the positive contaminants appear to lay down from the inlet to the outlet so that a forward flush may very well merely spread the deposited contaminants from the fouled inlet to the relatively less fouled outlet.

The flow of regeneration wash liquid was then stopped, and the reactor was back-flushed with hot nitrogen, at about 150° C., for about 15 hours to remove residual regeneration wash liquid from the catalyst.

After the back-flush with nitrogen, the reactor was switched back to the cracking mode. After regeneration, the cracking was conducted by reintroducing the hydrocarbon fluid feedstream in the vapor phase, through the reactor over the regenerated catalyst and the cracking outlet temperature needed for a preferred 95% conversion was established. In this regard, it was determined that the desired 95% conversion could be accomplished over the regenerated catalyst at a reduced cracking outlet temperature within the range of about 145° C.-150° C. The resultant feedstream for the distillation column consists essentially of 95% isoamylene, i.e. 2MB1 and 2MB2 in a ratio between 1:2 to 5 and preferably 1:5, and unreacted TAME and is then fed to a distillation column 20 which is preferably operated to vaporize the isoamylene. The vaporized overhead 22 is composed of isoamylene including 2MB1 and 2MB2. The unreacted TAME may be withdrawn as a bottoms fraction 26 and recycled through line 10a to be reintroduced to the cracking reactor 14 in feedstream 10.

Subsequent to regeneration, the regenerated catalyst has been observed to perform well after regeneration and may be successfully regenerated after, for example about 1700 hours, by again back-flushing with liquid TAME for about 35 hours and then with hot nitrogen for about 20 hours, in a manner consistent with the previously described procedure.

EXAMPLE I

A feed of TAME, analyzed at three times during the run as follows:

TABLE 1

TAME Feed Analyses

| Component | wt. % | | |
|---|---|---|---|
| | A | B | C |
| Methanol | 0.127 | 0.111 | 0.172 |
| C5's (hydrocarbon) | 0.310 | 0.310 | 0.177 |
| C6's (hydrocarbon) | 1.750 | 2.118 | 1.076 |
| TAME | 94.35 | 94.51 | 96.56 |
| Tert. Amyl Alcohol | <1.3 | 0.542 | 0.421 |
| Isoprene Ethers | 0.037 | 0.041 | 0.024 |
| Pentadiene Ethers | 0.290 | 0.213 | 0.082 |
| n-Heptane | 1.300 | 1.327 | 0.271 |
| Unknown Unsat $C_6$ Ether | — | — | 0.085 | was initially vaporized and super heated in a 12" long ⅛" OD (0.41" ID) tube wrapped with electrical heating tape. The effluent from the preheater then entered the reactor which was a ⅞" OD (0.61" ID) tube packed with catalyst in a Linberg furnace having a 12" long heating zone. The surface temperature of the heating element was controlled and the process temperature out of the catalyst bed monitored with a thermal coupler placed about ¼" to ½" above the catalyst bed. The reactor was configured for upflow. The reactor effluent was condensed with chilled water (10° C.–15° C.) and collected. The reactor temperature was set with a back-pressure regulator located between the product condenser and the product receiver.

The reactor was loaded with about 57 cm³ of the catalyst (38.6 grams), the packed bed depth being about 28.5 cm. The feed pump was set for a feed rate of about 105 cc hr., which corresponds to an LHSV=1.85-1. The back-pressure regulator on the reactor was set at 100K Pa. The preheater process outlet temperature was typically about 180° C.–190° C. and the cracker process outlet temperature was controlled to maintain about 95% TAME disappearance.

As shown in FIG. 2, the process temperature for 95% conversion is plotted against run time for the entire test. Legend for FIG. 2:
1. Hydrogenated TAME.
1A. Hydrogenated TAME with 35% to 2MB2 & 2MB1 (50/50 mix).
1B. Hydrogenated TAME with 3% MeOH.
2. Pure TAME from isoamylenes.
3. Hydrogenated TAME.
3A, B, C, D. Additional batches of hydrogenated TAME (3).
4. 50/50 blend of 1 & 2 above.

As can be seen, throughout most of this example, the temperature needed for about 95% conversion rose gradually. At about 1,300 hours the fouling became more erratic.

At 1,540 the catalyst regeneration procedure of the present invention was started and carried out in accordance with the procedure described above. In this regard, the vapor feed to the reactor was stopped and the reactor was cooled. The liquid TAME feed was re-routed to enter the reactor at the outlet and passed through the preheater (also outlet to inlet) and to the product receiver. The reactor and preheater were back-flushed in this manner with liquid TAME at 40° C.–50° C. and at the same feed rate as during normal cracking. The back-flush of regeneration wash liquid was continued for about 50 hours during which the effluent was observed to be initially dark brown, and became lighter in color until it was almost as clear as tap water after about 30 to 40 hours. The back flush of regeneration wash liquid was then stopped and the unit was back-flushed with hot nitrogen, at about 150° C., for about 15 hours to remove any residual regeneration wash liquid from the catalyst. After this procedure, the unit was switched back to the cracking mode and the cracking outlet temperature needed for 95% conversion was established.

As shown in FIG. 2, the back-flush with regeneration wash liquid was successful in reducing the cracking outlet temperature from about 159° C. to about 145° C. which demonstrates that the catalyst run length can be extended by back-flushing with regeneration wash liquid as liquid TAME.

The advantages realized by the regeneration procedure of the present invention are unexpected inasmuch as attempts which have been made at regenerating the catalyst using only hot $N_2$ were not particularly effective, and attempts made to regenerate the catalyst using concurrent flow of hot methanol vapor and a liquid TAME-methanol mix, were also not particularly successful. In all of these tests, however, the regenerating wash fluid was passed through the heater first and entered the reactor at the inlet. Although not wishing to be bound by any particular theory, it is believed that using a forward or concurrent flow of regeneration wash fluid could have carried polymer or other material from the preheater into the reactor which caused the temperature in the reactor to rise thereby leading to contamination of the catalyst. Thus, it would appear that back-flushing the reactor containing the deactivated catalyst with the regeneration washing liquid, preferably followed by back-flushing with $N_2$ is important to ensure that the contaminants which foul the active sites of the catalyst are removed.

Moreover, the regeneration procedure in accordance with the present invention is particularly advantageous in that the deactivated catalyst can be regenerated in situ in the reactor. Inasmuch as it is difficult to remove the catalyst from the reactor for this purpose, this advantage is directly related to improving the run length of the catalyst activity before the catalyst in the reactor must be replaced by new catalyst.

It is further understood that although the invention has been specifically described with reference to particular means and embodiments, the foregoing description is that of preferred embodiments of the invention. The invention, however, is not limited to the particulars disclosed but extends to all equivalents, and various changes and modifications may be made in the invention without departing from the spirit and scope thereof.

We claim:

1. A process for regenerating a deactivated ether decomposition catalyst fouled with deposited polymer in situ in a catalytic decomposition reactor, said process comprising:

washing a deactivated ether decomposition catalyst having active sites fouled with deposited olefin derived foulant polymer in situ in an ether decomposition reactor with a liquid selected from the group consisting of ethers, alcohols, and mixtures of ethers and alcohols at a temperature within the range of about 40° C. and 80° C. for a time less than about 50 hours to remove deposited polymer and recover substantial catalyst activity so as to result in a regenerated ether decomposition catalyst whereby the temperature required during decomposition using the regenerated ether decomposition catalyst is about 10° C.–15° C. lower than the upper temperature required during ether decomposition using said deactivated catalyst.

2. The process of claim 1 for regenerating a deactivated ether decomposition catalyst in situ in an ether decomposition reactor, wherein, prior to said washing, said process comprises decomposing a fluid stream comprising ethers over an ether decomposition catalyst in an ether decomposition reactor under conditions sufficient to support a reaction for converting said at least one member to a product comprising olefins for a time until product temperature at the reactor outlet increases to a temperature indicative of a deactivated ether decomposition catalyst.

3. The process of claim 2 for regenerating a deactivated ether decomposition catalyst in situ in an ether decomposition reactor, wherein said washing is performed by back-flushing said ether decomposition reactor containing said deactivated ether decomposition catalyst with said liquid.

4. The process of claim 3 for regenerating a deactivated ether decomposition catalyst in situ in an ether decomposition reactor, further comprising back-flushing said ether decomposition reactor with $N_2$ gas after said washing with said liquid.

5. The process of claim 1 for regenerating a deactivated ether decomposition catalyst in situ in an ether decomposition reactor, wherein said ether decomposition catalyst comprises a clay treated with an acid selected from the group consisting of hydrofluoric acid, hydrochloric acid and mixtures of hydrofluoric acid and hydrochloric acid.

6. The process of claim 5 for regenerating a deactivated ether decomposition catalyst in situ in a catalytic an ether decomposition reactor, wherein said ether decomposition catalyst comprises a clay treated with an acid selected from the group consisting of about 1.0%–70 wt. % hydrofluoric acid, about 1.0–37 wt. % hydrochloric acid and mixtures of about 1.0%–70 wt. % hydrofluoric acid and about 1.0%–37 wt. % hydrochloric acid.

7. The process of claim 6 for regenerating a deactivated ether decomposition catalyst in situ in an ether decomposition reactor, wherein said clay reacted with said acid is calcined.

8. The process of claim 7 for regenerating a deactivated ether decomposition catalyst in situ in an ether decomposition reactor, wherein said clay reacted with said acid is dried prior to being calcined.

9. The process of claim 4 for regenerating a deactivated ether decomposition catalyst in situ in an ether decomposition reactor, wherein said ether decomposition catalyst comprises a clay treated with hydrofluoric acid.

10. The process of claim 4 for regenerating a deactivated ether decomposition catalyst in situ in an ether decomposition reactor, wherein said clay is selected from the group consisting of montmorillonite, kaolinite, attapulgite, bentonite, and natural clay.

11. The process of claim 10 for regenerating a deactivated ether decomposition catalyst in situ in an ether decomposition reactor, wherein said clay is a natural clay.

12. The process of claim 10 for regenerating a deactivated ether decomposition catalyst in situ in an ether decomposition reactor, wherein said clay is attapulgus clay.

13. The process of claim 10 for regenerating a deactivated ether decomposition catalyst in situ in an ether decomposition reactor, wherein said clay is montmorillonite clay.

14. The process of claim 10 for regenerating a deactivated ether decomposition catalyst in situ in an ether decomposition reactor, wherein said catalyst has a surface area above 40 $M^2$/gm.

15. The process of claim 14 for regenerating a deactivated ether decomposition catalyst in situ in an ether decomposition reactor, wherein said surface area is within the range of about 70 $M^2$/gm to about 400 $M^2$/gm.

16. The process of claim 14 for regenerating a deactivated ether decomposition catalyst in situ in an ether decomposition reactor, wherein said liquid is an ether.

17. The process of claim 16 for regenerating a deactivated ether decomposition catalyst in situ in an ether decomposition reactor, wherein said ether is a tertiary alkyl ether.

18. The process of claim 17 for regenerating a deactivated ether decomposition catalyst in situ in an ether decomposition reactor, wherein said tertiary alkyl ether is a member selected from the group consisting of tertiary amyl methyl ether and methyl tertiary butyl ether.

19. The process of claim 18 for regenerating a deactivated ether decomposition catalyst in situ in an ether decomposition reactor, wherein said tertiary alkyl ether is tertiary amyl methyl ether.

20. The process of claim 18 for regenerating a deactivated ether decomposition catalyst in situ in an ether decomposition reactor, wherein said tertiary alkyl ether is methyl tertiary butyl ether.

21. The process of claim 14 for regenerating a deactivated ether decomposition catalyst in situ in an ether decomposition reactor, wherein said liquid is an alcohol.

22. The process of claim 21 for regenerating a deactivated ether decomposition catalyst in situ in an ether decomposition reactor, wherein said alcohol is a member selected from the group consisting of tertiary amyl alcohol, tertiary butyl alcohol, methanol, and a mixture of at least two members selected from the group consisting of tertiary amyl alcohol, tertiary butyl alcohol, and methanol.

23. The process of claim 22 for regenerating a deactivated ether decomposition catalyst in situ in an ether decomposition reactor, wherein said alcohol is methanol.

* * * * *